United States Patent
Yang

(10) Patent No.: US 9,383,301 B2
(45) Date of Patent: Jul. 5, 2016

(54) METHOD AND DEVICE FOR LOADING SPECIMENS INTO TENSILE TESTING MACHINE

(71) Applicant: Shih-Liang Stanley Yang, Laguna Hills, CA (US)

(72) Inventor: Shih-Liang Stanley Yang, Laguna Hills, CA (US)

(*) Notice: Subject to any disclaimer, the term of this patent is extended or adjusted under 35 U.S.C. 154(b) by 0 days.

(21) Appl. No.: 14/499,204

(22) Filed: Sep. 28, 2014

(65) Prior Publication Data

US 2016/0091402 A1 Mar. 31, 2016

(51) Int. Cl.
*G01N 3/02* (2006.01)
*G01N 3/08* (2006.01)

(52) U.S. Cl.
CPC ... *G01N 3/02* (2013.01); *G01N 3/08* (2013.01)

(58) Field of Classification Search
CPC ............. G01N 3/04; G01N 3/08; G01N 3/02; G01N 33/38; G01N 2203/0278
USPC ............................. 73/750, 856, 860, 760, 827
See application file for complete search history.

(56) References Cited

U.S. PATENT DOCUMENTS

| | | | | |
|---|---|---|---|---|
| 3,721,119 A * | 3/1973 | Strimel | ..................... | G01N 3/08 73/816 |
| 3,789,660 A * | 2/1974 | Rubio | ..................... | G01N 3/14 73/169 |
| 3,885,424 A * | 5/1975 | Ryckman | .................. | G01N 3/04 73/800 |
| 4,606,230 A * | 8/1986 | Scott | ........................ | G01N 3/02 73/826 |
| 5,224,386 A * | 7/1993 | Curtis | ....................... | G01N 3/04 73/833 |
| 2012/0258469 A1* | 10/2012 | Babu | ..................... | G01N 33/558 435/7.4 |

* cited by examiner

*Primary Examiner* — Max Noori
(74) *Attorney, Agent, or Firm* — Che-Yang Chen; Law Offices of Scott Warmuth

(57) ABSTRACT

A sample loading device may include a top plate and a base plate, and the sample loading device can be roughly divided into two portions: a loading portion and a holding portion. The present invention is advantageous because the test sample is introduced by the sample loading device, which has been designed for a standard T-peel test, so the integrity of the sample introducing process will not be affected even though a different operator is conducting the process. Furthermore, it is easy to for the operator to load the test sample to the sample loading device, as well as transferring the sample loading device to the tensile testing machine, so the errors during the sample loading process can be significantly reduced. In other words, the T-peel test results can be more reliable when the test sample is introduced by the sample loading device in the present invention.

17 Claims, 7 Drawing Sheets

METHOD AND DEVICE FOR LOADING SPECIMENS INTO TENSILE TESTING MACHINE

FIELD OF THE INVENTION

The present invention relates to a sample loading device, and more particularly to a sample loading device for introducing a test sample into a tensile testing machine.

BACKGROUND OF THE INVENTION

Numerous test methods exist for characterizing adhesives and bonded joints, and may be used to determine fatigue resistance, environmental durability and creep behavior. Adhesive tests can be divided into those methods that provide mechanical property data for the adhesive, which aids the selection of adhesives, and those methods that can be used to determine the quality of adhesively bonded structures, and thus aid the design process of adhesive joints.

An ASTM F88/F88M-09 test method is a standard test method for seal strength of flexible barrier materials, which covers the measurement of the strength of seals in flexible barrier materials. The test may also be conducted on seals between a flexible material and a rigid material. This test method measures the force required to separate a test strip of material containing the seal. It also identifies the mode of specimen failure, and seals tested in accordance with this test method may be from any source, laboratory or commercial.

Seal strength is a quantitative measure for use in process validation, process control, and capability. Seal strength is not only relevant to opening force and packaging integrity, but to measuring the packaging processes' ability to produce consistent seals. Seal strength at some minimum level is a necessary packaging requirement, and at times it is desirable to limit the strength of the seal to facilitate opening.

One of the testing machines is of the constant rate-of-jaw-separation type. The machine shall be equipped with a weighing system that moves a maximum distance of 2% of the specimen extension within the range being measured. The machine shall be equipped with a device for recording the tensile load and the amount of separation of the grips. It is noted that both of these measuring systems shall be accurate to ±2%. The rate of separation of the jaws shall be uniform and capable of adjustment from approximately 8 to 12 inches [200 to 300 mm]/min. The gripping system shall be capable of minimizing specimen slippage and applying an even stress distribution to the specimen. It is noted that if calculation of average seal strength is required, the testing machine system shall have the capability to calculate its value over a specific range of grip travel programmable by the operator. Preferably, the machine shall have the capability also to plot the curve of force versus grip travel.

Among the test methods used to determine the seal strength of an adhesive including peel, shear, cleavage, and tension tests, peel tests are common for tapes, labels, coatings, and other bonded materials, which measure the force required to separate a test strip of material containing the seal. If the test strip peels apart in the seal area, either by adhesive failure, or cohesive failure, the average peel force is an important index of performance of the performance of the seal.

While performing the test, the tensile testing machine has to be calibrated. The test specimens are then prepared by cutting to the dimensions in accordance with the test method, such as shown in FIG. 1. It is noted that edges should be clean-cut and perpendicular to the direction of the seal. Specimen wings may be shorter than shown, depending on the grip dimension of the testing machine.

The test specimen is then transferred to the testing machine by clamping each wing of the test specimen in the testing machine. The sealed area of the specimen shall be appropriately equidistant between the grips. The specimen should also be centered laterally and aligned in the grips, so the seal line is perpendicular to the direction of pull, allowing sufficient slack so the seal is not stressed prior to initiation of the test.

According to the test results, the orientation of a fin-seal tail during the test is a major factor to affect the measurement of the seal strength. It is critical that the specimen is precisely positioned in the grips of the testing machine because the testing results can vary significantly if the specimen is not properly and precisely positioned in the grips. Operators may manually load the specimens into a tensile testing machine and visually check the orientations and positions of the specimens in the grips, which may usually lead to errors due to improper or inconsistent loading operations, and the testing results may be adversely affected. Therefore, there remains a need for a new and improved method and apparatus for consistent and precise loading of the specimens.

SUMMARY OF THE INVENTION

It is an object of the present invention to provide a method and device to consistently and precisely load the specimens into a tensile testing machine.

It is another object of the present invention to provide a method and device to consistently and precisely load the specimen into a tensile testing machine to significantly reduce the errors occurred due to improper loading operations.

In one aspect, a sample loading device may include a top plate and a base plate. In one embodiment, the top plate and the base plate can be coupled together by screws through a plurality of screw holes on the top and base plates. The sample loading device can be roughly divided into two portions: a loading portion and a holding portion. The thickness of the loading portion and the holding portion is substantially equal to the combined thickness of the top plate and base plate. In one embodiment, a receiving groove is formed at nearly the center portion of the loading portion to receive a test sample. In another embodiment, the loading portion and holding portion can be made as one piece. In still another embodiment, the loading portion is detachable from the holding portion.

In an exemplary embodiment, the test sample is a T-type specimen having a sealed portion and two wing-shaped portions. When loading the test sample into the sample loading device, the wing portions can be flatly disposed on a protruding portion of the base plate, and an edge (other than the one held by the user's hand) of the sealed portion is aligned with the receiving groove at nearly the center of the loading portion. Furthermore, a gap is formed between the top plate and a base plate, so that the test sample can be slid into the loading portion of the sample loading device.

When transferring the test sample to the tensile testing machine, the user holds the holding portion of the sample loading device and deliver the test sample into the space between the first and second grips, wherein one wing portion of the test sample is slid into a first grip gap, while the other wing portion is slid into a second grip gap. It is noted that the loading process will be completed once a stopping edge touches a loading side of the first and second grips, and a first knob and a second knob are used to secure the wing portions by tightening the grips.

Once the grips are tightened, the user can remove his/her hand from the holding portion and further remove the sample loading device from the test sample, and the test sample can be properly secured between two grips and the seal strength test can be conducted.

The present invention is advantageous because the test sample is introduced by a sample loading device, which has been designed for the standard seal strength test, so the integrity of the sample introducing process will not be affected even though a different operator is conducting the process. Furthermore, it is easy to for the operator to load the test sample to the sample loading device, as well as transferring the sample loading device to the tensile testing machine, so the errors during the sample loading process can be significantly reduced. In other words, the seal strength test results can be more reliable and consistent when the test sample is introduced by the sample loading device in the present invention.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Figure 1:
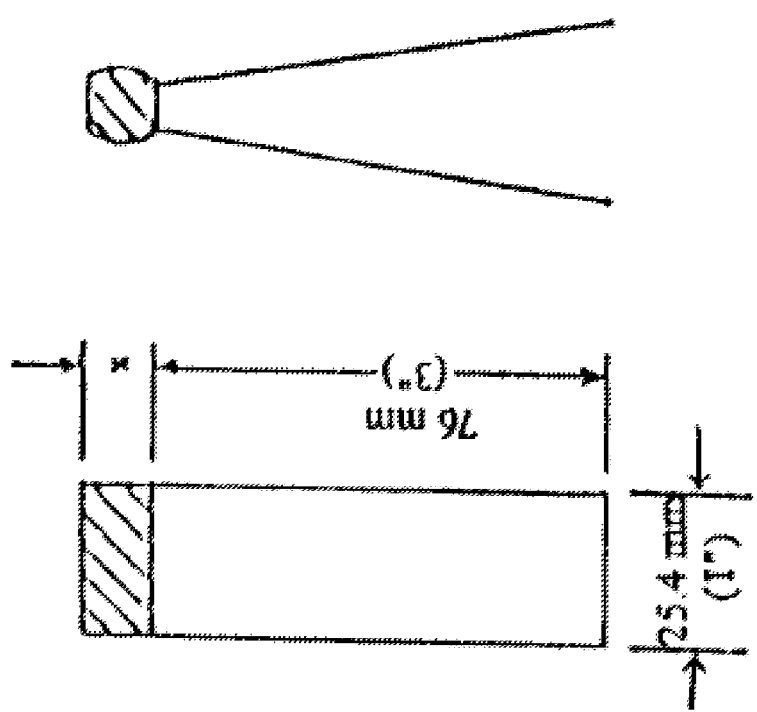
FIG. 1 illustrates a schematic view of a test sample for a seal strength test in the present invention.
Figure 2:
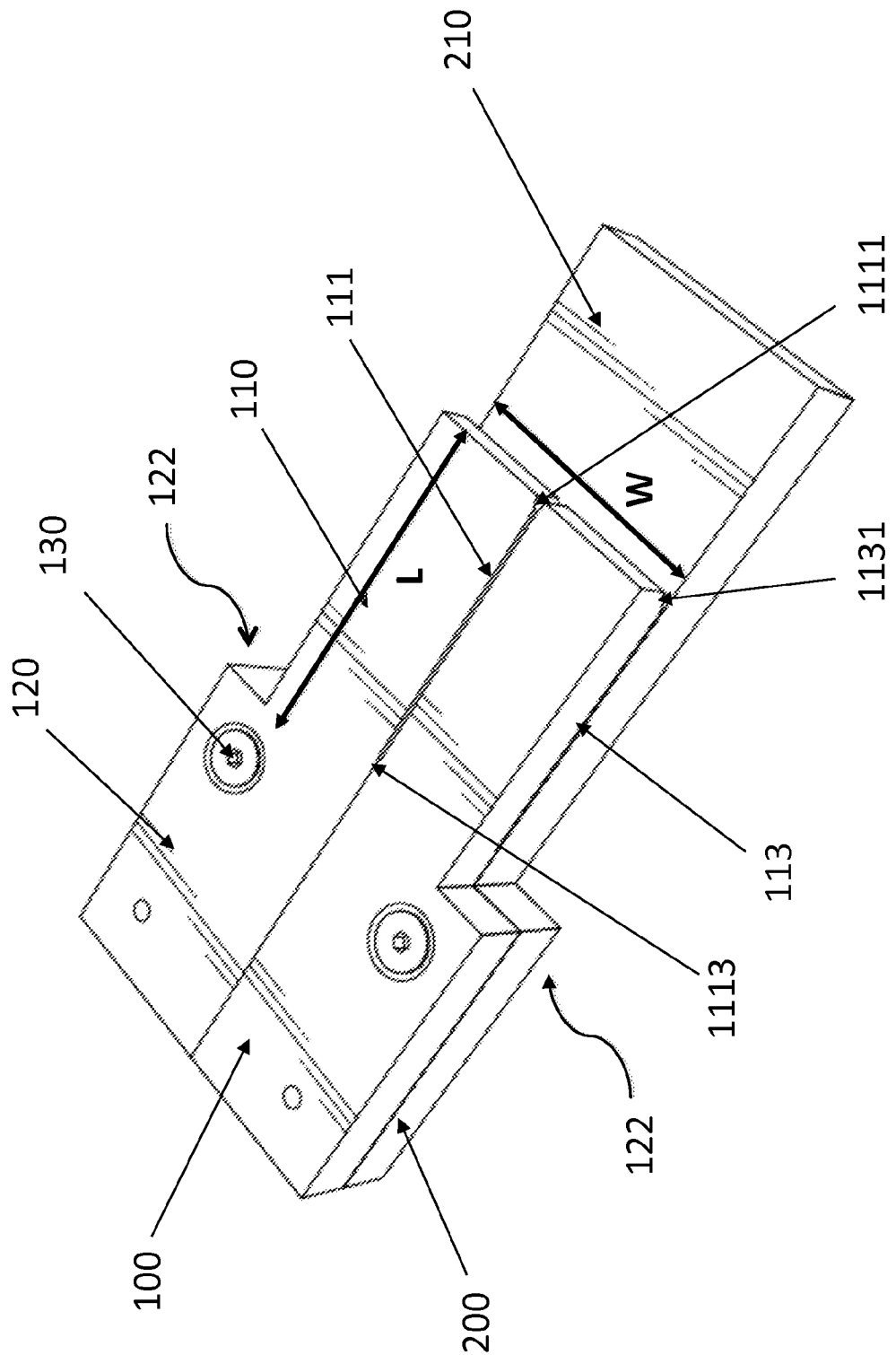
FIG. 2 illustrates a top view of a sample loading device in the present invention.
Figure 3:
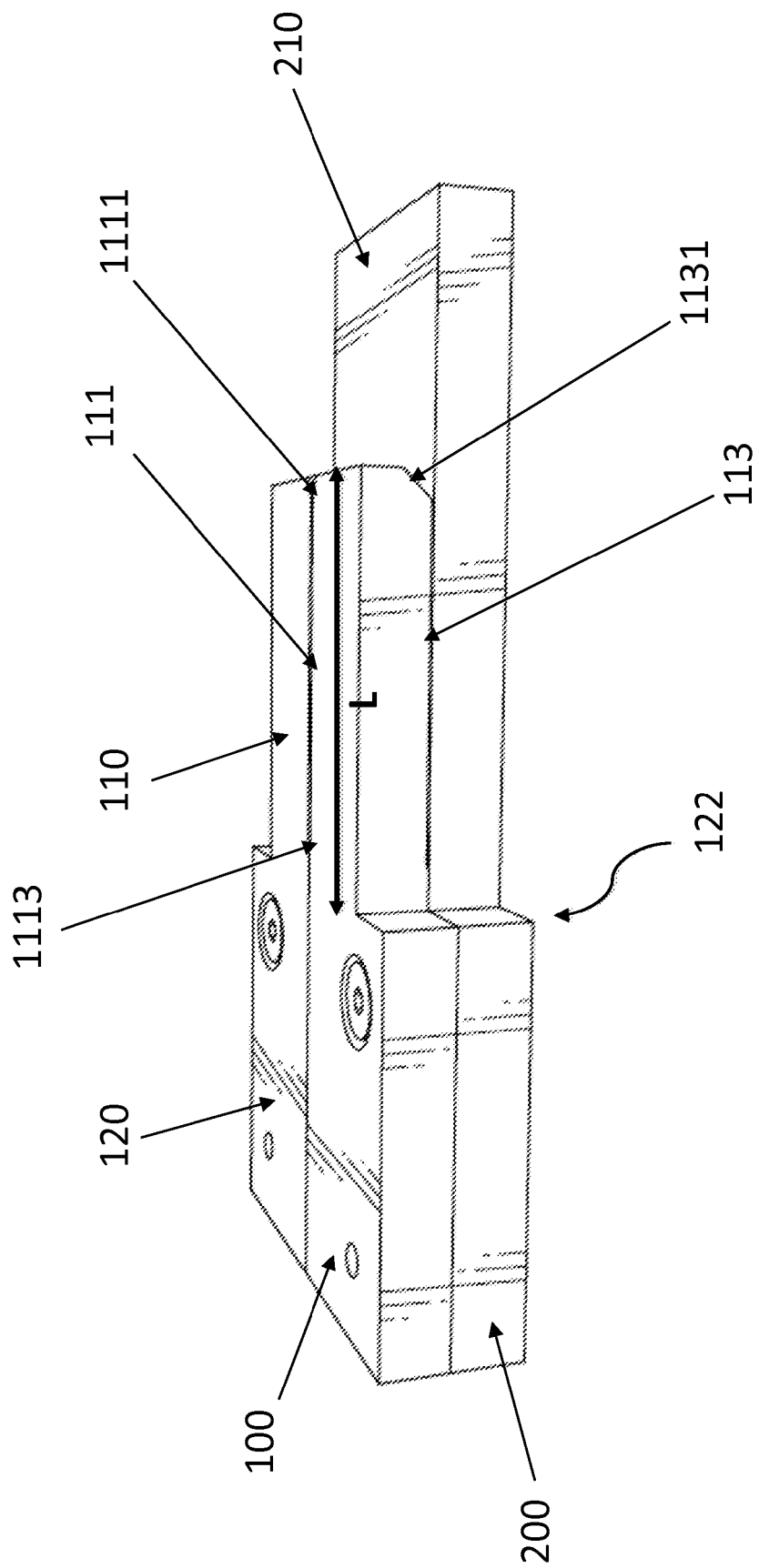
FIG. 3 illustrates a lateral view of a sample loading device in the present invention.
Figure 4:
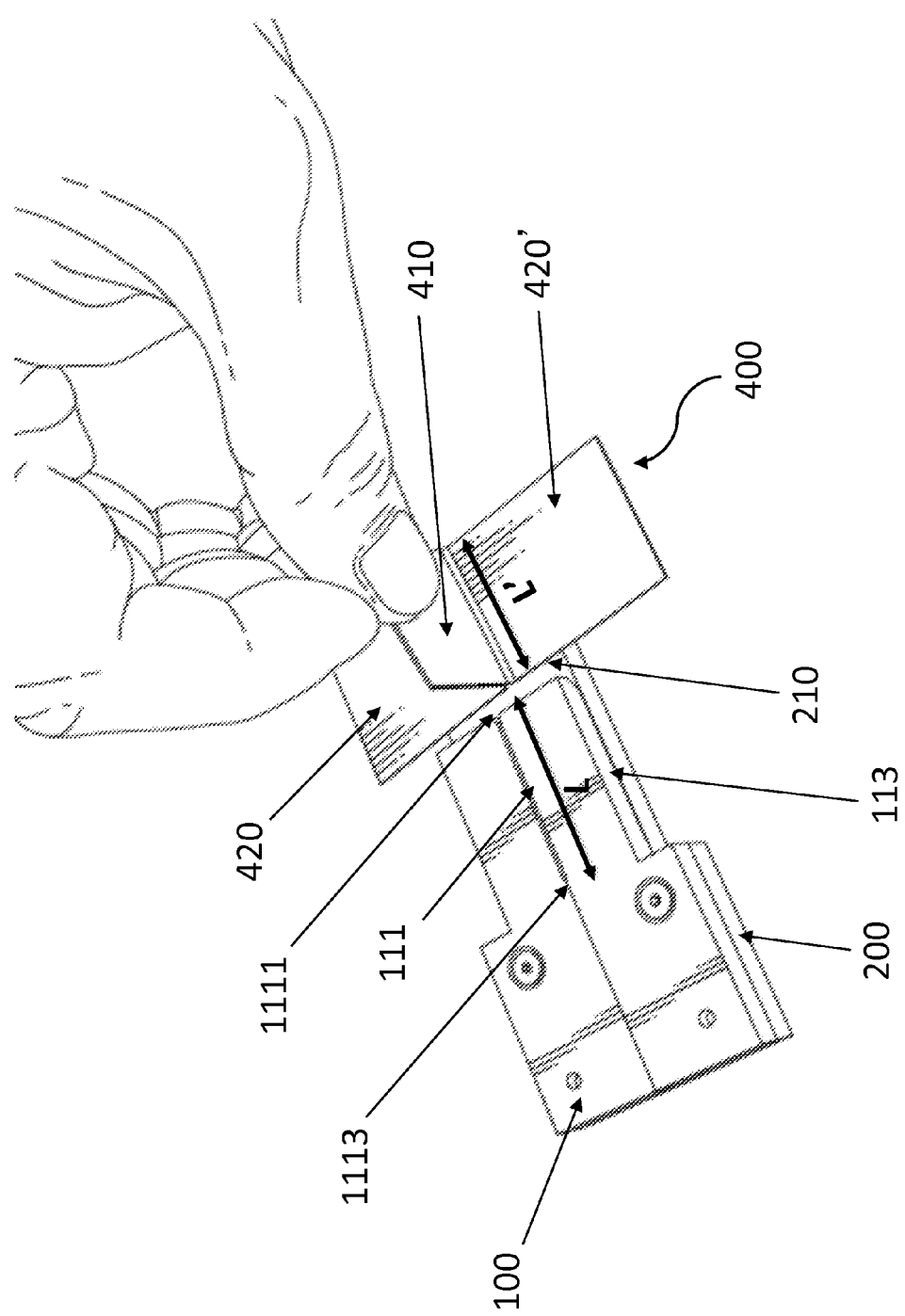
FIG. 4 illustrates a schematic view of the present invention when a T-shaped specimen is being slid into the sample loading device.

Referring to FIGS. 2 and 3, a sample loading device may include a top plate 100 and a base plate 200. In one embodiment, the top plate 100 and the base plate 200 can be coupled together by screws through a plurality of screw holes 130. The sample loading device can be roughly divided into two portions: a loading portion 110 and a holding portion 120. The thickness of the loading portion 110 and the holding portion 120 is substantially equal to the combined thickness of the top plate 100 and base plate 200. A receiving groove 111 is formed at nearly the center portion of the loading portion 110 to receive a test sample 400. In one embodiment, the receiving groove 111 may be formed a predetermined distance away from the center portion of the loading portion 110. In another embodiment, the loading portion 110 and holding portion 120 can be made as one piece. In a further embodiment, the loading portion 110 is detachable from the holding portion 120, and the holding portion 120 may be formed in one piece. In an exemplary embodiment, the test sample 400 is a T-type specimen as shown in FIG. 4.

Conventionally, as discussed above, operators may manually load the specimens into a tensile testing machine and visually check the orientations and positions of the specimens in the grips of the testing machine. As a result, errors may occur due to improper or inconsistent loading operations. Also, the testing results (for the same specimen) may vary due to the operator's loading preference. As shown in FIG. 4, the test sample 400 has a sealed portion 410 and two wing portions 420 and 420'. When loading the test sample 400 into the sample loading device, the wing portions 420 and 420' can be flatly disposed on a protruding portion 210 of the base plate 200, and an edge (other than the one held by the user's hand) of the sealed portion 410 is aligned with the receiving groove 111. Furthermore, a gap 113 is formed between the top plate 100 and a base plate 200 (see FIGS. 2 and 3), so that the test sample 400 can be slid into the loading portion 110 of the top plate 100.

It is noted that the width of the receiving groove 111 is slightly greater than the width of the sealed portion 410 of the test sample 400, and the width of the gap 113 is slightly greater than the thickness of the wing portions 420 and 420', so the test sample 400 can be smoothly slid into the loading portion 110. Also, as shown in FIGS. 2 and 3, the entering point 1111 has a slightly wider opening, and a bottom portion of the loading portion 110 close to the gap 113 has a gap entering point 1131 that is cut inwardly to better receive the sample 400. It is also noted that the receiving groove has an entering point 1111 and a stopping point 1113. The test sample 400 is actually slid into the receiving groove 111 from the entering point 1111, and being stopped at the stopping point 1113, and the distance from the entering point 1111 to the stopping point 1113, namely the length (L) of the receiving groove 111, is substantially equal to or greater than the length (L') of the edge (of the sealed portion 410) held by the user's hand.

After the test sample 400 is properly positioned in the sample loading device, the test sample 400 along with the sample loading device are transferred to a tensile testing machine 500 for a "seal strength test." The tensile testing machine 500 has a first grip 510 and a second grip 510', which are vertically and spacedly disposed on the tensile test machine 500. In one embodiment, the space between the first and second grips (510, 510') is substantially equal to the width (W) of the loading portion 110 of the sample loading device.

Figure 5:
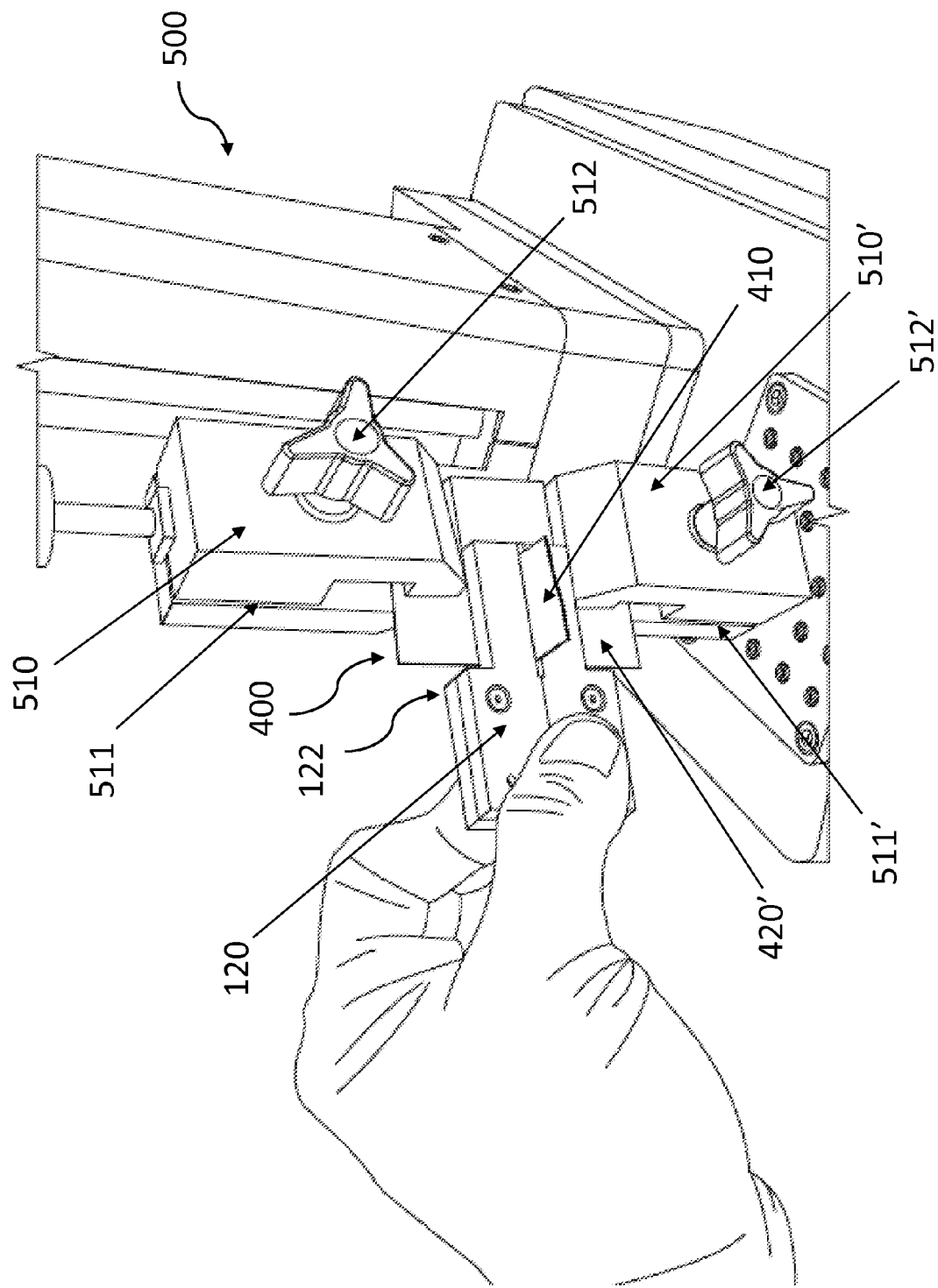
FIG. 5 illustrates a schematic view of the present invention when the sample loading device with the T-shaped specimen are transferred to a tensile testing machine.

As shown in FIG. 5, when the test sample 400 is loaded to the tensile testing machine 500, the user holds the holding portion 120 of the sample loading device and delivers the test sample 400 into the space between the first and second grips (510, 510'), wherein one wing portion 420 of the test sample 400 is slid into a first grip gap 511, while the other wing portion 420' is slid into a second grip gap 511'. It is noted that the loading process will be completed once a stopping edge 122 touches a loading side of the first and second grips (510, 510'), and a first knob 512 and a second knob 512' are used to secure the wing portions 420 and 420' respectively by tightening the grips (510, 510').

Figure 6:
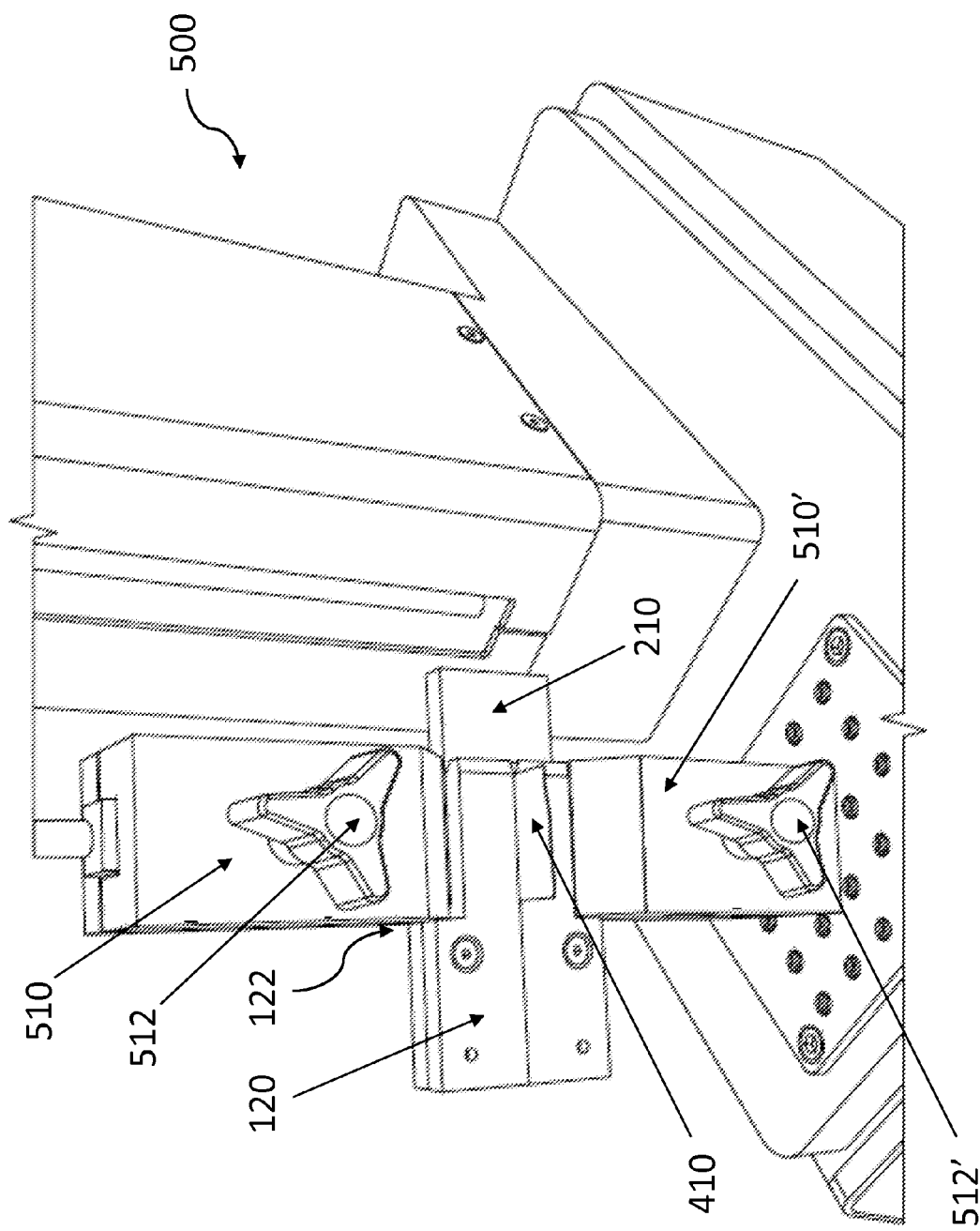
FIG. 6 illustrates a schematic view of the present invention when the sample loading device with the T-shaped specimen are secured to a tensile testing machine.
Figure 7:
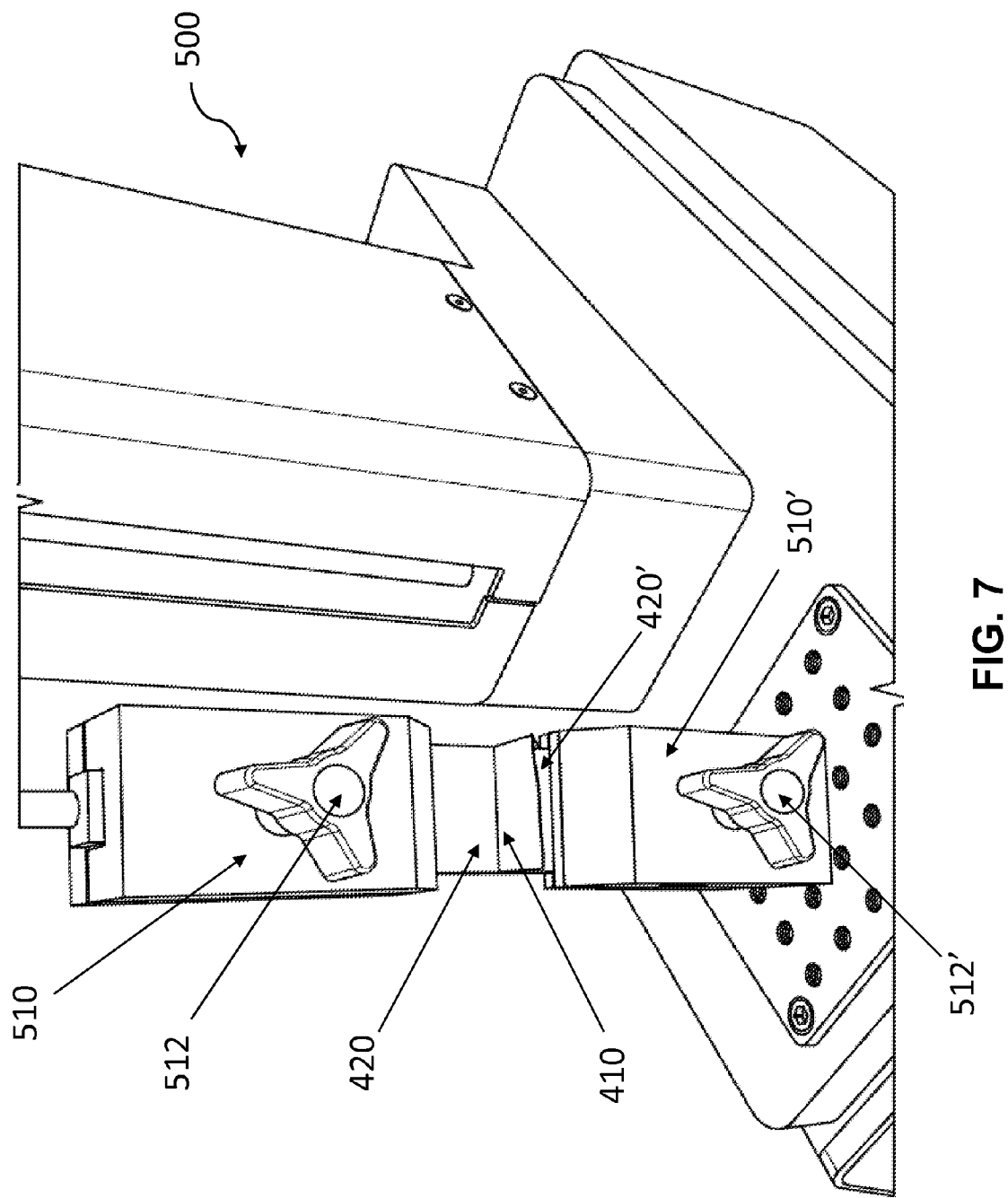
FIG. 7 illustrates a schematic view of the present invention when the T-shaped specimen is secured to a tensile testing machine after removing the sample loading device.

As shown in FIGS. 6 and 7, once the grips (510, 510') are tightened, the user can remove his/her hand from the holding portion 120 and further remove the sample loading device from the test sample 400, and the test sample can be properly secured between two grips (510, 510') and the seal strength test can be conducted. It is noted that the width (513, 513') of the first and second grips (510, 510') respectively is substantially equal to the length (L) of the holding portion 110 of the sample loading device. In an exemplary embodiment, the length (L) of the holding portion 110 can be defined as the distance between the stopping edge 122 and the entering point 1111 of the receiving grove 111.

Conventionally, as stated above, the operator may have to manually introduce the test sample 400 into the tensile testing machine 500. More specifically, the operator has to manually position two wing portions (420, 420') into the first and second grips (510, 510'). Even though it does not seem to be a complicated task, the operator can only manually adjust the test sample 400 and visually check the orientations and positions of the specimens in the grips. As a result, errors may occur due to imprecise or inconsistent loading operation, which may adversely affect the seal strength testing results. Thus, the present invention is advantageous because the test sample 400 is introduced by a sample loading device, which has been designed for the standard seal strength test, so the integrity of the sample introducing process will not be affected even though a different operator is conducting the process. Furthermore, it is easy to for the operator to load the test sample 400 to the sample loading device, as well as transferring the sample loading device to the tensile testing machine 500, so the errors during the sample loading process can be significantly reduced. In other words, the seal strength test results can be more reliable and consistent when the test sample is introduced by the sample loading device in the present invention.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A sample loading device for measuring the seal strength in flexible barrier materials comprising a loading portion and a holding portion, said the loading portion having a top plate and a base plate, said loading portion having a receiving groove on the top plate, and a gap formed on the loading portion between the top plate and the base plate, wherein the loading portion is configured to receive and hold a test sample with a predetermined configuration, and holding portion is configured to be held by hand to transfer the loaded test specimen to a tensile testing machine, wherein the test sample is a T-type specimen having a sealed portion and two wing portions extending from one end of the sealed portion, wherein the receiving groove is formed at a predetermined distance from a center portion of the top plate of the loading portion to receive the sealed portion of the T-type specimen, while the wing portions are slid into the gap on the loading portion between the top plate and base plate, wherein the sealed portion of test sample is slid into the receiving groove from an entering point, and being stopped at a stopping point, and a distance from the entering point to the stopping point, namely the length of the receiving groove, is substantially equal to or slightly greater than the length of an edge of the sealed portion of the T-type specimen.

2. The sample loading device of claim 1, wherein the loading portion and holding portion are made as one piece.

3. The sample loading device of claim 1, wherein the loading portion is detachable from the holding portion.

4. The sample loading device of claim 1, wherein the test sample received by the sample loading device is disposed in a space between a first grip and a second grip of the tensile testing machine, and one wing portion of the test sample is slid into a first grip gap of the first grip, while the other wing portion is slid into a second grip gap of the second grip.

5. The sample loading device of claim 4, further includes a stopping edge to stop the loading device at a loading side of the first and second grips so that the wing portions of test sample are inserted centrally within the grips, and the first and second grip are tightened by a first knob and a second knob respectively to further secure the wing portions therein.

6. The sample loading device of claim 5, wherein the sample loading device is removed from the test sample and a seal strength test is conducted to the test sample.

7. The sample loading device of claim 4, wherein the space between a first grip and a second grip of the tensile testing machine is substantially equal to the width of the loading portion of the sample loading device.

8. The sample loading device of claim 1, wherein the receiving groove is at the center portion of the top plate of the loading portion.

9. The sample loading device of claim 1, wherein the entering point of the receiving grove has a slightly wider opening, and the gap has a gap entering point that is located at a bottom portion of the top plate is cut inwardly to better receive the test sample.

10. The sample loading device of claim 5, wherein the length of the holding portion is defined as a distance between the stopping edge and the entering point of the receiving grove, and the width of each of the first and second grips is substantially equal to the length of the holding portion of the sample loading device.

11. A method for loading a test sample to a tensile testing machine for measuring the seal strength in flexible barrier materials comprising steps of:

preparing for a test sample in a "T-configuration" with a sealed portion and two wing portions extending from one end of the sealed portion;

providing a sample loading device, which comprises a loading portion and a holding portion, said the loading portion having a top plate and a base plate, said loading portion having a receiving groove on the top plate, and a gap formed on the loading portion between the top plate and the base plate, wherein the loading portion is configured to receive and hold a test sample with a predetermined configuration, and holding portion is configured to be held by hand to transfer the loaded test sample to the tensile testing machine;

sliding the test sample into the sample loading device, wherein the receiving groove is formed at a predetermined distance from a center portion of the top plate of the loading portion to receive the sealed portion of the "T-configuration" test sample, while the wing portions are slid into the gap on the loading portion between the top plate and base plate;

transferring the sample loading device with the test sample to the tensile testing machine, wherein the test sample received by the sample loading device is disposed in a space between a first grip and a second grip of the tensile testing machine, and one wing portion of the test sample is slid into a first grip gap of the first grip, while the other wing portion is slid into a second grip gap of the second grip;

centering the test sample laterally in the grips and aligning the test sample in the grips so a seal line of the sealed portion is perpendicular to the direction to remove the sample loading device;

tightening up the first and second grips to secure the test sample on the tensile testing machine; and removing the sample loading device.

12. The method for loading a test sample to a tensile testing machine for measuring the seal strength in flexible barrier materials of claim 11, wherein the sealed portion of test sample is slid into the receiving groove from an entering point, and being stopped at a stopping point, and a distance from the entering point to the stopping point, namely the length of the receiving groove, is substantially equal to or slightly greater than the length of an edge of the sealed portion of the "T-configuration" test sample.

13. The method for loading a test sample to a tensile testing machine for measuring the seal strength in flexible barrier materials of claim 11, wherein the loading portion and holding portion are made as one piece.

14. The method for loading a test sample to a tensile testing machine for measuring the seal strength in flexible barrier materials of claim 12, wherein the entering point of the receiving grove has a slightly wider opening, and the gap has a gap entering point that is located at a bottom portion of the top plate is cut inwardly to better receive the test sample.

15. The method for loading a test sample to a tensile testing machine for measuring the seal strength in flexible barrier materials of claim 11, wherein the sample loading device further includes a stopping edge to stop the loading device at a loading side of the first and second grips so that the wing portions of test sample are inserted centrally within the grips.

16. The method for loading a test sample to a tensile testing machine for measuring the seal strength in flexible barrier materials of claim 11, wherein the loading portion is detachable from the holding portion.

17. The method for loading a test sample to a tensile testing machine for measuring the seal strength in flexible barrier materials of claim 11, wherein the receiving groove is at the center portion of the top plate of the loading portion.

* * * * *